United States Patent
Yokoyama et al.

(10) Patent No.: US 8,771,784 B2
(45) Date of Patent: Jul. 8, 2014

(54) METHOD FOR PRODUCING COATING HAVING DESIRED GLOSS VALUE

(75) Inventors: Ayumu Yokoyama, Clarkston, MI (US); Rajesh Gopalan Saliya, Media, PA (US); Sheau-Hwa Ma, West Chester, PA (US)

(73) Assignee: Axalta Coating Systems IP Co., LLC, Wilmington, DE (US)

( * ) Notice: Subject to any disclaimer, the term of this patent is extended or adjusted under 35 U.S.C. 154(b) by 80 days.

(21) Appl. No.: 13/377,613

(22) PCT Filed: May 5, 2010

(86) PCT No.: PCT/US2010/033690
§ 371 (c)(1),
(2), (4) Date: Dec. 12, 2011

(87) PCT Pub. No.: WO2011/014284
PCT Pub. Date: Feb. 3, 2011

(65) Prior Publication Data
US 2012/0094012 A1    Apr. 19, 2012

Related U.S. Application Data

(60) Provisional application No. 61/229,880, filed on Jul. 30, 2009, provisional application No. 61/229,884, filed on Jul. 30, 2009, provisional application No. 61/229,890, filed on Jul. 30, 2009.

(51) Int. Cl.
*B05D 3/02* (2006.01)
*G01N 21/57* (2006.01)
*B05D 5/02* (2006.01)
*B05D 5/06* (2006.01)
*C09D 7/00* (2006.01)
*G01J 3/50* (2006.01)

(52) U.S. Cl.
CPC ...... *G01N 21/57* (2013.01); *B05D 5/02* (2013.01); *B05D 5/061* (2013.01); *C09D 7/005* (2013.01); *G01J 3/504* (2013.01)
USPC ............ 427/8; 427/407.1; 427/408; 427/409; 427/412.1

(58) Field of Classification Search
None
See application file for complete search history.

(56) References Cited

U.S. PATENT DOCUMENTS

| | | | | |
|---|---|---|---|---|
| 5,146,097 A | * | 9/1992 | Fujiwara et al. | 250/372 |
| 5,760,122 A | * | 6/1998 | Susa et al. | 524/493 |
| 6,331,582 B1 | * | 12/2001 | Chen et al. | 523/400 |

(Continued)

FOREIGN PATENT DOCUMENTS

EP    761778    *    3/1997

OTHER PUBLICATIONS

Fletcher, Progress in Organic Coatings, 44, pp. 25-36, 2002.*

(Continued)

*Primary Examiner* — Erma Cameron
(74) *Attorney, Agent, or Firm* — Ingrassia Fisher & Lorenz, P.C.

(57) ABSTRACT

The present invention is directed to a method for producing a coating having a desired gloss value on a substrate. This invention is also directed to method for producing a predicted gloss value of a coating on a substrate. This invention is further directed to a method of using a matting agent comprising components derived from renewable resources.

21 Claims, 6 Drawing Sheets

(56) References Cited

U.S. PATENT DOCUMENTS

| | | | |
|---|---|---|---|
| 6,461,689 B1 * | 10/2002 | Gauthier et al. | 427/494 |
| 6,720,459 B2 * | 4/2004 | Sunkara et al. | 568/619 |
| 6,977,291 B2 * | 12/2005 | Sunkara et al. | 528/425 |
| 7,158,672 B2 | 1/2007 | Johansson et al. | |
| 2003/0235683 A1 * | 12/2003 | Tamagawa et al. | 428/195.1 |
| 2012/0189764 A1 * | 7/2012 | Yokoyama et al. | 427/8 |
| 2013/0141713 A1 * | 6/2013 | Saliya et al. | 356/36 |
| 2013/0141724 A1 * | 6/2013 | Yokoyama et al. | 356/402 |

OTHER PUBLICATIONS

White et al, Industrial and Engineering Chemistry, vol. 33 No. 9, pp. 1169-1173, 1941.*

Gunde et al, Dyes and Pigments, 74, pp. 202-207, 2007.*

Trezza, T.A., et al. "Specular Reflection, Gloss, Roughness and Surface Heterogeneity of Biopolymer Coatings," Journal of Applied Polymer Science, 2001, p. 2221-2229, vol. 79.

* cited by examiner

METHOD FOR PRODUCING COATING HAVING DESIRED GLOSS VALUE

CROSS-REFERENCE TO RELATED APPLICATION

This application claims priority under 35 U.S.C. §119 from U.S. Provisional Application Ser. No. 61/229,880 (filed on Jul. 30, 2009), U.S. Provisional Application Ser. No. 61/229,884 (filed on Jul. 30, 2009), and U.S. Provisional Application Ser. No. 61/229,890 (filed on Jul. 30, 2009).

FIELD OF INVENTION

The present invention is directed to a method for producing a coating having a desired gloss value on a substrate. This invention is also directed to method for producing a predicted gloss value of a coating on a substrate.

BACKGROUND OF INVENTION

Consumers' and industrial desires on coating appearance are diversified. Sometimes, a preference is given to coatings having low gloss or low luster. These desires present challenges to coating industry for producing coatings that have varied appearances including low gloss or low luster with reduced shining, reflecting light, glitter, sparkle or sheen. For some industrial or transportation uses, anti-glare coatings having very low gloss are desired. Typically, such coatings with low gloss are produced by incorporating a matting agent, also known as a flattener, which imparts matting effect into a coating composition. The matting agent can comprise inorganic particles, such as silicon compound particles. Typically, gloss value of a coating is measured after the coating is produced. Currently, repeated testing and trial are needed to produce a coating having a desired gloss value. Coating manufacturers are typically providing a series of premixed coating products that each can be used to produce a coating having a certain range of gloss values. Such premixed coating products lack flexibility, especially when a desired gloss value is not covered by the premixed coating products.

STATEMENT OF INVENTION

This invention is directed to a method for producing a coating having a target gloss value on a substrate, said coating is formed from a coating composition and a matting agent, said method comprising steps of:
  a) obtaining a gloss-mixing ratio correlation data system that comprises correlations of gloss values to mixing ratios of said matting agent and said coating composition;
  b) generating a target mixing ratio of said matting agent and said coating composition according to said target gloss value and said gloss-mixing ratio correlation data system;
  c) producing a coating mixture comprising said coating composition and said matting agent having said target mixing ratio; and
  d) producing said coating by applying said coating mixture over said substrate.

This invention is also directed to a method for producing a predicted gloss value of a coating on a substrate, said coating is formed from a coating composition and a matting agent, said method comprising the steps of:
  a) obtaining a gloss-mixing ratio correlation data system that comprises correlations of gloss values to mixing ratios of said matting agent and said coating composition;
  b) providing a target mixing ratio;
  c) producing said predicted gloss value according to said gloss-mixing ratio correlation data system and said target mixing ratio; and
  d) outputting said predicted gloss value to an output device.

This invention is further directed to a coating system for producing a coating having a target gloss value on a substrate, said coating system comprising:
  a) a coating composition;
  b) a matting agent; and
  a) a gloss-mixing ratio correlation data system that comprises correlations of gloss values to mixing ratios of said matting agent and said coating composition;

wherein said coating is produced from a coating mixture comprising said coating composition and said matting agent according to a target mixing ratio, said target mixing ratio being determined according to said target gloss value and said gloss-mixing ratio correlation data system.

BRIEF DESCRIPTION OF DRAWING

FIG. 1 shows examples of gloss-mixing ratio correlation data system. (A) Gloss-weight mixing ratio for a white color coating. (B) Gloss-volume mixing ratio for the white color coating.

FIG. 2 shows further examples of gloss-mixing ratio correlation data system, (A) Gloss-weight mixing ratio for an orange color coating. (B) Gloss volume mixing ratio for the orange color coating.

FIG. 3 shows further examples of gloss-mixing ratio correlation data system. (A) Gloss-weight mixing ratio for a yellow color coating. (B) Gloss-volume mixing ratio for the yellow color coating, FIG. 4 shows further examples of gloss-mixing ratio correlation data system. (A) Gloss-weight mixing ratio for a red color coating, (B) Gloss-volume mixing ratio for the red color coating, FIG. 5 shows further examples of gloss-mixing ratio correlation data system, (A) Gloss-weight mixing ratio for a black color coating. (B) Gloss-volume mixing ratio for the black color coating.

FIG. 6 shows further examples of gloss-mixing ratio correlation data system. (A) Gloss-weight mixing ratio for all color coatings, (B) Gloss-volume mixing ratio for the all color coatings.

DETAILED DESCRIPTION

The features and advantages of the present invention will be more readily understood, by those of ordinary skill in the art, from reading the following detailed description. It is to be appreciated that certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both proceeded by the word "about." In this manner, slight variations above and below the stated ranges can be used to achieve substantially the same results as values within the ranges. Also, the disclosure of these ranges is intended as a continuous range including every value between the minimum and maximum values.

As used herein:

"Gloss" means surface gloss of a coating surface and is related to the amount of incident light that is reflected at the specular reflectance angle of the mean of that surface. Gloss can be measured with a specular glossmeter, such as those available from Byk-Gardener, Geretsried, Germany.

"DOI" (Distinctness of Image) is a quantitative measure of coating appearance that measures the light reflected at and around the specular reflectance angle. It can be determined according to the method described in ASTM D 5767. DOI can be measured with wave scan instruments, such as those available from Byk-Gardener, Geretsried, Germany. DOI measures not only the amount of incident Eight that is reflected at the specular reflectance angle, but also the distribution of the reflected light around the reflectance specular angle, typically +/−0.3 from the specular angle. A coating surface that gives fuzzy or distorted image generally produces lower DOI reading. A coating reflecting 100% of lights at the Specular angle gives a DOI reading of 100.

The term "vehicle", "automobile" or "automobile vehicle" refers an automobile; truck; semitruck; tractor; motorcycle; trailer; ATV (all terrain vehicle); pickup truck; heavy duty mover, such as, bulldozer, mobile crane and earth mover; airplanes; boats; ships; and other modes of transport. A typical vehicle body or part thereof can be produced from a steel sheet or a plastic or a composite substrate. For example, the fenders can be of plastic or a composite and the main portion of the body of steel.

A "database" used herein refers to a collection of related information that can be searched and retrieved. The database can be a searchable electronic text document, a searchable PDF document, an Microsoft Excel® spreadsheet, a plot having a plurality of related data points, a chart of plurality of related data points, an Microsoft Access® database (both supplied by Microsoft Corporation of Redmond, Wash.), an Oracle® database (supplied by Oracle Corporation of Redwood Shores, Calif.), or a Lynux database, each registered under their respective trademarks. The database can be a set of electronic documents, photographs, images, diagrams, or drawings, residing in a computer readable storage media that can be searched and retrieved. A database can be a single database or a set of related databases or a group of unrelated databases, "Related database" means that there is at least one common information element in the related databases that can be used to relate such databases, The term "output device" can include, but not limited to, a computer monitor, a projector, a TV screen, a personal digital assistant (PDA) device, a cell phone, a smart phone that combines PDA and cell phone, an iPod, iPod/MP Player, a flexible thin display, or any other devices that can display or output information or images based on digital signals. The display device can also be a printing device that prints, based on digital signals, information or image onto papers, plastics, textiles, or any other surfaces that are suitable for printing the information or images onto. The output device can also be a duel functional display/data input device, such as a touch screen. The output device can also be a piece of conventional paper or plotting paper.

The term "two-pack coating composition" or "2K coating composition" or "2K coating system" refers to a coating composition having two packages that are stored in separate containers and sealed to increase the shelf life of The coating composition during storage. The two packages are mixed just prior to use to form a pot mix, also known as a coating mixture, which has a limited pot life, typically ranging from a few minutes (15 minutes to 45 minutes) to a few hours (4 hours to 8 hours). The pot mix is then applies as a layer of a desired thickness on a substrate surface, such as an automobile body. After application, the layer dries and cures at ambient or at elevated temperatures to form a coating on the substrate surface having desired coating properties, such as, adhesion, gloss, and DOl.

The term "one-pack coating composition" or "1K coating composition" or "1K coating system" refers to a coating composition having one package that can be stored for a certain shelf life. For example, a 1K coating composition can be a radiation curable coating composition, such as a UV mono-cure coating composition that can be prepared to form a pot mix and stored in a sealed container. As long as the UV mono-cure coating composition is not exposed to UV radiation, it can have indefinite pot life. Other examples of 1K coating composition can include 1K coating compositions having blocked crosslinking agent such as blocked isocyanates, moisture curing 1K coating compositions, oxygen curing 1K coating compositions, or heat curing 1K coating compositions as known in coating industry, The term "crosslinkable component" refers to a component having "crosslinkable functional groups" that are functional groups positioned in each molecule of the compounds, oligomer, polymer, the backbone of the polymer, pendant from the backbone of the polymer, terminally positioned on the backbone of the polymer, or a combination thereof, wherein these functional groups are capable of crosslinking with crosslinking functional groups (during the curing step) to produce a coating in the form of crosslinked structures. One of ordinary skill in the art would recognize that certain crosslinkable functional group combinations would be excluded, since, if present, these combinations would crosslink among themselves (self-crosslink), thereby destroying their ability to crosslink with the crosslinking functional groups. A workable combination of crosslinkable functional groups refers to the combinations of crosslinkable functional groups that can be used in coating applications excluding those combinations that would self-crosslink.

Typical crosslinkable functional groups can include hydroxyl, thiol, isocyanate, thioisocyanate, acetoacetoxy, carboxyl, primary amine, secondary amine, epoxy, anhydride, ketimine, aldimine, or a workable combination thereof. Some other functional groups such as orthoester, orthocarbonate, or cyclic amide that can generate hydroxyl or amine groups once the ring structure is opened can also be suitable as crosslinkable functional groups.

The term "crosslinking component" refers to a component having "crosslinking functional groups" that are functional groups positioned in each molecule of the compounds, oligomer, polymer, the backbone of the polymer, pendant from the backbone of the polymer, terminally positioned on the backbone of the polymer, or a combination thereof, wherein these functional groups are capable of crosslinking with the crosslinkable functional groups (during the curing step) to produce a coating in the form of crosslinked structures. One of ordinary skill in the art would recognize that certain crosslinking functional group combinations would be excluded, since, if present, these combinations would crosslink among themselves (self crosslink), thereby destroying their ability to crosslink with the crosslinkable functional groups. A workable combination of crosslinking functional groups refers to the combinations of crosslinking functional groups that can be used in coating applications excluding those combinations that would self-crosslink. One of ordinary skill in the art would recognize that certain combinations of crosslinking functional group and crosslinkable functional groups would be excluded, since they would fail to crosslink and produce the film forming crosslinked structures. The crosslinking component can comprise one or more crosslinking agents that have the crosslinking functional groups. A coating composition comprising a crosslinkable component and a crosslinking component can also be referred to as a chemical curable coating composition.

Typical crosslinking functional groups can include hydroxyl, thiol, isocyanate, thioisocyanate, acetoacetoxy, carboxyl, primary amine, secondary amine, epoxy, anhydride, ketimine, aldimine, orthoester, orthocarbonate, cyclic amide or a workable combination thereof.

The term "powder coating composition" or "powder coating" refers to a type of coating that can be applied as a free-flowing, dry powder. A powder coating typically does not require a solvent.

The term "lacquer coating composition", "lacquer coating" or "lacquer" refers to a coating composition that dries via solvent evaporation without any substantial crosslinking of the binder of the coating composition. Typically, a lacquer coating composition can dry to form a coating layer and does not require a crosslinking component. A lacquer coating composition can, however, further comprise an additional crosslinking component that can typically reduce curing time and improve coating properties. Conventional method is to mix the lacquer with a crosslinking component in the way similar to the 2 k coating composition.

The coating composition can also comprise protected crosslinkable groups and a crosslinking component. In one example, the protected crosslinkable groups are selected from the group consisting of amide acetal, orthocarbonate, orthoester, spiroorthoester, orthosilicate, oxazolidine and combinations thereof. In one example, the crosslinking component can comprise a compound, oligomer or polymer having crosslinking groups selected from the group consisting of isocyanate, amine, ketimine, melamine, epoxy, carboxylic acid, anhydride, and a combination thereof. Due to the presence of the protected crosslinkable functional groups, the crosslinkable and the crosslinking groups typically can not initiate crosslinking reaction. The protected crosslinkable groups can be activated by introducing an activator such as water or water with acid.

The term "matting agent" refers to a composition that can be used to reduce or control gloss of coatings. A matting agent can comprise inorganic particles, such as silica particles. The silica particles can have an average particle size in a range of from 2 to 20 micrometers (μm). The silica particles can have different surface treatment. In one example, the silica particles are organic surface treated silica particles. In another example, silica particles, are untreated. In yet another example, the silica particles are thermally treated. Silica particles can have hydrophobic or hydrophilic surface property. Matting agents comprise commercial available silica particles, such those available under the trademark ACEMATT® from marketed Degussa Evonik, can be suitable for this invention, Silica particles that have organic surface-treatment, such as ACEMATT® OK 412 can also be suitable. Commercial available matting agent, such as Imron® Industrial Strength 9T20™ Flattener available from DuPont, Wilmington, USA, under respective registered or unregistered trademarks, can also be suitable. The matting agent is typically formulated to be compatible to the coating composition that it is intended to provide matting. For example, for a solvent borne coating composition, the matting agent is typically also formulated in solvent and is compatible with the solvent borne coating composition. Techniques for formulating matting agents are known to those skilled in the art Matting agent can also comprise polytrimethylene ether diol. Suitable polytrimethylene ether dial can have a number average molecular weight (Mn) in the range of from 500 to 10,000, preferably 500 to 8,000, even preferably 500 to 4,000. The polytrimethylene ether dial can have a Tg of about −75° C., a polydispersity in the range of from 1.1 to 2.1 and a hydroxyl number in the range of from 20 to 200. Suitable polytrimethylene ether dial can be prepared by an acid-catalyzed polycondensation of 1,3-propanediol, such as described in U.S. Pat. Nos. 6,977,291 and 6,720,459. A bio-route via fermentation of a renewable resource can be used to obtain the 1,3-propanediol. One example of renewable resources is corn since it is readily available and has a high rate of conversion to 1,3-propanediol and can be genetically modified to improve yields to the 1,3-propanediol. Examples of typical bio-route can include those described in U.S. Pat. No. 5,686,276, U.S. Pat. No. 5,633,362 and U.S. Pat. No. 5,821,092.

The matting agent can comprise one or more solvents if so desired. Any typical organic solvents commonly used in coating industry can be suitable for this invention. Examples of solvents can include, but not limited to, aromatic hydrocarbons, such as, toluene, xylene; ketones, such as, acetone, methyl ethyl ketone, methyl isobutyl ketone, methyl amyl ketone and diisobutyl ketone; esters, such as, ethyl acetate, n-butyl acetate, isobutyl acetate and a combination thereof. Some commercial available solvents, such as Oxsol® 100 available from MANA, New York, N.Y., USA, under respective registered trademark, can also be used.

This invention is directed to a method for producing a coating having a target gloss value on a substrate, said coating is formed from a coating composition and a matting agent. The method can comprise the steps of:
  a) obtaining a gloss-mixing ratio correlation data system that comprises correlations of gloss values to mixing ratios of said matting agent and said coating composition;
  b) generating a target mixing ratio of said matting agent and said coating composition according to said target gloss value and said gloss-mixing ratio correlation data system;
  c) producing a coating mixture comprising said coating composition and said matting agent having said target mixing ratio; and
  d) producing said coating by applying said coating mixture over said substrate.

The gloss-mixing ratio correlation data system can be generated by a fitting process comprising the steps of:
  i) producing a first coating mixture comprising said coating composition and said matting agent according to a first mixing ratio $x_1$, applying the first coating mixture over a first substrate forming a dry first coating, and measuring a first gloss value $y_1$ of the dry first coating;
  ii) producing a second coating mixture comprising said coating composition and said matting agent according to a second mixing ratio $x_2$, applying the second coating mixture over a second substrate forming a dry second coating, and measuring a second gloss value $y_2$ of the dry second coating;
  iii) repeating the steps i) and ii) above for subsequent mixing ratios $x_3$ through $x_n$, and measuring subsequent gloss values $y_3$ through $y_n$; and iv) generating said gloss-mixing ratio correlation data system by fitting the mixing ratios $x_1$ through $x_n$ and the gloss values $y_1$ through $y_n$;

wherein, n is an integer equal to or greater than 3, and said gloss-mixing ratio correlation data system has a correlation coefficient $R^2$ equal to or greater than 0.7, Typically, the gloss-mixing ratio correlation data system can comprise 3 or more pairs of x and y values as described above. The gloss-mixing ratio correlation data system can be a gloss-mixing ratio plot chart in that said mixing ratios $x_1$ through $x_n$ and said gloss values $y_1$ through $y_n$ are plotted on an x-y chart and fitted to a fitting curve by any known mathematical functions that can provide the best fit to the $x_1$ through $x_n$ and $y_1$ through $y_n$ data points. One example of such mathematical functions can be polynomial curves fitting. The fitting curve generated based on the $x_1$ through $x_n$ and $y_1$ through $y_n$ data points can be displayed on the x-y chart. Another example can be manually drawing of a curve through all available data points on the x-y chart while keeping the sum of distance between the curve and each of the data points minimum. Based on the fitting curve and the correlation coefficient $R^2$, a y value or a range of y values can be obtained for a given x value, and vise versa.

The gloss-mixing ratio correlation data system can also be expressed as a 2-degree polynomial fitting equation. One example of such 2-degree polynomial fitting equation can be Formula (1) below:

$$y = a_1 x^2 + a_2 x + a_3 \qquad (1)$$

wherein y is a gloss value, x is a mixing ratio of coating composition and matting agent, $a_1$, $a_2$ and $a_3$ are constants determined through fitting said mixing ratios $x_1$ through $x_n$ and said gloss values $y_1$ through $y_n$. Based on Formula (1), a y value can be obtained by executing the equation for a given x value, and vise versa.

The gloss-mixing ratio correlation data system can also be expressed as other curve fitting mathematical functions or equations that can provide best fit to the x mixing ratios and y gloss values and have a preferred correlation coefficient $R^2$ as described below. Constants can be determined by those curve fitting mathematical functions or equations, It is preferred that the gloss-mixing ratio correlation data system has a correlation coefficient $R^2$ equal to or greater than 0.7, even preferred equal to or greater than 0.8. The correlation coefficient $R^2$ is the square of the correlation between the gloss values y and mixing ratios x, and can typically be a value between 0 and 1. The correlation coefficient $R^2$ can be determined mathematically based on the mixing ratios $x_1$ through $x_n$ and the gloss values $y_1$ through $y_n$ data.

The mixing ratio can be selected from a volume mixing ratio or a weight mixing ratio. In one example, the mixing ratio is a volume mixing ratio, such as the ratio of a volume of the matting agent/a volume of the coating composition. In another example, the mixing ratio is a weight mixing ratio, such as the ratio of a weight of the matting agent/a weight of the coating composition. The volume ratio and weight ratio can be converted to each other according to density of the coating composition and the matting agent, respectively.

For a coating composition that comprises multiple components, the gloss-mixing ratio can be calculated based on one or more, or all of the components. In one example, the coating composition can be a 2K coating composition comprising a crosslinkable component, a crosslinking component, and optionally, additional components such as catalyst, a reducer or additives. In this example, the mixing ratio can be calculated based on the matting agent and the crosslinkable component, or based on the matting agent and the total of the crosslinkable component and the crosslinking component, or based on all of the crosslinkable component, the crosslinking component and the additional components, In another example, the coating composition can be a 1K coating composition comprising a protected crosslinkable component and a crosslinking component. The mixing ratio can be calculated based on the matting agent and the total of the protected crosslinkable component and the crosslinking component. The mixing ratio can also be calculated based on the matting agent and only the protected crosslinkable component.

It is understood that mixing ratios in the gloss-mixing ratio correlation data system and the mixing ratios used to produce the coating system need to be consistent. That means if the a volume mixing ratio is desired for producing the coating mixture, then the gloss-mixing ratio correlation data system should comprise correlations of gloss values and that volume mixing ratios. Equally, if desired, the gloss-mixing ratio correlation data system can comprise correlations of gloss values and mixing ratios of the matting agent and a component of the coating composition.

The coating mixture can be produced based on the mixing ratio. The coating mixture can comprise other components such as an activator, an accelerator, a reducer, or other conventional coating additives. The activator can be a component that activates the coating composition to form a coating. The activator can be a crosslinking component of a two-pack coating composition, or a component such as water that activates the aforementioned protected crosslinkable component. The accelerator can be a component that increases coating formation process. The reducer can be a component that reduces viscosity of the coating composition. Typically, a reducer can be one or more solvents. Examples of conventional additives can include wetting agents, leveling and flow control agents, for example, Resiflow®S (polybutylacrylate), BYK® 320 and 325 (high molecular weight polyacrylates), BYK® 347 (polyether-modified siloxane) under respective registered tradmarks, leveling agents based on (meth)acrylic homopolymers; rheological control agents, such as highly disperse silica, or fumed silica; thickeners, such as partially crosslinked polycarboxylic acid or polyurethanes; and anti-foaming agents. The additives are used in conventional amounts familiar to those skilled in the art.

For a coating system having a plurality of colors, gloss-mixing ratio correlation data system can be based on data points from individual color or based on a collection of data points for a group of colors. The volume mixing ratio is preferred for the coating system having a plurality of colors and the gloss-mixing ratio data system comprising data points from said plurality of colors, In conventional practices known in the coating industry, gloss of a coating is typically measured after the coating is produced and dried. Conventional practices typically require repeated testing and trials to produce a coating having a desired gloss value. As a result, currently, coating manufacturers are typically providing a series of premixed coating products that each can be used to produce a coating having a certain range of gloss values. Such premixed coating products lack flexibility, especially when a desired gloss value is not covered by any of the premixed coating products.

Inventors of this application unexpectedly discovered that when a coating product is formulated into a coating composition and a matting agent compatible to that coating composition, a correlation between mixing ratios and gloss values of the resulted coating can be obtained. With the gloss mixing ratio correlation data system established and disclosed in this application, a coating having a targeted gloss value can be produced. The best correlation between the mixing ratio and the gloss can be achieved when correlation coefficient $R^2$ of the gloss-mixing ratio correlation data system is equal to or greater than 0.7. One advantage of this invention is that when a target gloss value is desired, a mixing ratio can be obtained based on the target gloss value and a coating can be produced based on that mixing ratio. Another advantage is that for a given mixing ratio, a gloss value can be predicted. Yet another advantage is that the gloss value and mixing ratio can be correlated using a plot chart, such as the aforementioned x-y chart, or a polynomial equation.

Yet another advantage of this invention is that a user can have the flexibility to produce coatings having desired gloss values with only one coating composition and one matting agent. With this invention, there is no need for multiple coating products having different gloss values. This can result in simplification of product lines for coating manufacturers and easy of use for coating users. For a coating system that has a plurality of colors, only one coating composition for each color can be needed with this invention.

The mixing ratio can be a volume mixing ratio or a weight mixing ratio. For a given set of coating composition and matting agent, either volume ratio or weight ratio can be suitable. The volume mixing ratio can be preferred for a coating system that has a plurality of coating compositions with different colors, particularly when the plurality of coating compositions has different densities. While not wishing to be bound by any particular theory, it is believed that matting effect of the matting agent could have higher correlation to pigment volume of the matting agent rather than the weight.

This invention is also directed to a method for producing a predicted gloss value of a coating on a substrate, said coating is formed from a coating composition and a matting agent. The said method comprising the steps of:
 a) obtaining a gloss-mixing ratio correlation data system that comprises correlations of gloss values to mixing ratios of said matting agent and said coating composition;
 b) providing a target mixing ratio;
 c) producing said predicted gloss value according to said gloss-mixing ratio correlation data system and said target mixing ratio; and
 d) outputting said predicted gloss value to an output device.

The gloss-mixing ratio correlation data system can be generated by the aforementioned fitting process either by plotting on an x-y chart or by fitting to a 2-degree polynomial equation. The mixing ratio can be volume mixing ratio or weight mixing ratio.

The predicted gloss value can be outputted onto a display device, or any aforementioned output devices. The plotting and curve fitting can also be done manually, such as on a piece of paper, based on available data points. The predicted gloss value can be produced from the fitted curve and outputted onto paper or any other media that can display or communicate the gloss value.

This invention is further directed to a coating system for producing a coating having a target gloss value on a substrate. The coating system comprising:
 a) a coating composition;
 b) a matting agent; and
 c) a gloss-mixing ratio correlation data system that comprises correlations of gloss values to mixing ratios of said matting agent and said coating composition;
wherein said coating is produced from a coating mixture comprising said coating composition and said matting agent according to a target mixing ratio, said target mixing ratio being determined according to said target gloss value and said gloss-mixing ratio correlation data system. The gloss-mixing ratio correlation data system can have a correlation coefficient $R^2$ equal to or greater than 0.7, preferred equal to or greater than 0.8.

The coating system can comprise a plurality of coating compositions. For example, each of the plurality of coating compositions can have a different color. Each can be mixed with the matting agent at a mixing ratio according to the gloss-mixing ratio correlation data system for producing the coating having the desired gloss.

The coating system can have the advantage of producing a wide range of desired gloss values by mixing at different mixing ratios of one coating composition and one matting agent. Conventionally, coating manufacturers provide a coating system having multiple coating products each having different gloss range, such as flat, semi, and high gloss. With this invention, coatings having a specific gloss value can be produced by simply mixing, at a certain mixing ratio, of one coating composition and one matting agent. The mixing ratio can be determined from the gloss-mixing ratio correlation data system described in this invention. This can significantly simplify product lines of coating manufacturers and provide flexibility for users to produce coatings having desired gloss values.

The coating composition can be selected from a solvent borne coating composition or a waterborne coating composition. The coating composition can also be selected from a two-pack coating composition or a one-pack coating composition. The coating composition can further be selected from a chemical curable coating composition, a radiation curable coating composition, or a chemical and radiation dual cure coating composition.

The coating composition can be a chemical durable coating composition that comprises a crosslinkable component and a crosslinking component as mentioned before, The coating composition can be a 1K coating composition or a 2K coating composition. The coating composition can also be a mono-cure such, as a chemical curable coating composition or a radiation curable coating composition; or a dual-cure coating composition, such as a chemical and radiation dual-cure coating composition.

The coating composition can be a powder coating composition. Any powder coating compositions known to one skilled in the art can be suitable for this invention, The coating composition can also be a lacquer coating composition, The coating composition can also comprise protected crosslinkable groups and a crosslinking component. The protected crosslinkable groups can be activated by introducing an activator such as water or water with acid. The activator can be added to the coating mixture. When appropriate, activators such as water can also be absorbed from the moisture in the air, The matting agent can be formulated to be compatible with the coating composition. The matting agent can comprise silica. The matting agent can further comprise a polytrimethylene ether diol having a Mn (number average molecular weight) in a range of from 500 to 10,000. It is preferred that the polytrimethylene ether diol is polymerized from bio-derived 1,3-propanediol.

The substrate can be selected from metal, wood, plastic, composite, or a combination thereof. The substrate can also be selected from a vehicle body, vehicle body part, or a combination thereof.

The substrate can also be an article. Some examples of the article can include, but not limited to: home appliances, such as refrigerators, washing machines, dishwashers, microwave ovens, cooking and baking ovens; electronic appliances, such as television sets, computers, electronic came sets, audio and video equipments; recreational equipments, such as bicycles, ski equipments, all terrain vehicles; and home or office furniture, such as tables, file cabinets.

Testing Procedures

Dry Film Thickness—test method ASTM D4138

Gloss—measured with standard test method for specular gloss according to ASTM D 523. Gloss can be measured with a specular glossmeter, such as those available from Byk-Gardener, Geretsried, Germany. Gloss value measurement can be shown in gloss unit (GU) with values ranging from 1 being low gloss to 100 being high gloss.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of invention, and without departing from the spirit and scope thereof, can make various changes and modifications of the invention to adapt it to various uses and conditions.

Examples 1-22

Gloss Value and Mixing Ratio

Coating mixtures were prepared by mixing coating compositions and matting agents according to Table 1-Table 5. The coating mixtures were applied over cold roll steel with Bonderite®1000 available from ACT Test Panel Technoiodes, Hillsdale, Mich., USA, by drawdown with a blade Cat number PA-2041 available from BYK Instrument, Columbia, Md., USA. Average dry film thickness of the coatings was about 45±5 microns. Banderite® is a registered trademark of Parker Rust Proof Company Corporation, Detroit Mich. The coating was cured at ambient temperature for about 60 min. Gloss values of the thy coatings were measured according to Testing Procedures with an average of 3 readings at 60-degree angle for each data point.

Weight mixing ratios were calculated based on the Formula (2):

Weight Mixing Ratio=Matting Agent Party by Weight/Colored Coating Component Part by Weight.

Volume mixing ratios were calculated by the Formula (3):

Volume Mixing Ratio=(Matting Agent Part by Weight/Matting Agent Density)/(Color Coating Component Part by Weight/Color Coating Component Density)

wherein densities of the coating compositions and the matting agent are listed in Table 6.

TABLE 1

White Color Coating Mixture and Gloss Data

|  | Ex. 1 | Ex. 2 | Ex. 3 | Ex. 4 |
|---|---|---|---|---|
| White coating component[1] (Part by Weight) | 7.5 | 7.5 | 7.5 | 7.5 |
| Matting Agent[2] (Part by Weight) | 5.5 | 7.0 | 8.5 | 10.0 |
| Coating Activation component[3] | 1.8 | 1.8 | 1.8 | 1.8 |

TABLE 1-continued

White Color Coating Mixture and Gloss Data

|  | Ex. 1 | Ex. 2 | Ex. 3 | Ex. 4 |
|---|---|---|---|---|
| Coating Accelerator component[4] | 0.3 | 0.3 | 0.3 | 0.3 |
| Weight Mixing Ratio | 0.73 | 0.93 | 1.13 | 1.33 |
| Volume Mixing Ratio | 0.72 | 0.92 | 1.11 | 1.31 |
| Gloss at 60° | 35.4 | 3.7 | 1.5 | 1.5 |

[1]White coating component was Imron ® Industrial Strength White 9T01 ™, available from DuPont, Wilmington, USA, under respective registered or unregistered trademarks.
[2]Matting agent was Imron ® Industrial Strength Flattener 9&20 ™, available from DuPont, Wilmington, USA, under respective registered or unregistered trademarks.
[3]Coating Activation component was 9T00-A ™, available from DuPont, Wilmington, USA, under respective trademarks.
[4]Coating Accelerator component was VG805 ™, available from DuPont, Wilmington, USA, under respective trademarks.

TABLE 2

Orange Color Coating Mixture and Gloss Data.

|  | Ex. 5 | Ex. 6 | Ex. 7 | Ex. 8 |
|---|---|---|---|---|
| Orange coating component[5] (Part by Weight) | 7.5 | 7.5 | 7.5 | 7.5 |
| Matting Agent[2] (Part by Weight) | 5.5 | 7.0 | 8.5 | 10.0 |
| Coating Activation component[3] | 1.8 | 1.8 | 1.8 | 1.8 |
| Coating Accelerator component[4] | 0.3 | 0.3 | 0.3 | 0.3 |
| Weight Mixing Ratio | 0.73 | 0.93 | 1.13 | 1.33 |
| Volume Mixing Ratio | 0.61 | 0.77 | 0.94 | 1.10 |
| Gloss at 60° | 42.7 | 10.8 | 1.5 | 1.0 |

[5]Orange coating component was Imron ® Industrial Strength Orange 9T13 ™, available from DuPont, Wilmington, USA, under respective registered or unregistered trademarks.
[2]-[4]Same as that in Table 1.

TABLE 3

Yellow Color Coating Mixture and Gloss Data.

|  | Ex. 9 | Ex. 10 | Ex. 11 | Ex. 12 |
|---|---|---|---|---|
| Yellow coating component[6] (Part by Weight) | 7.5 | 7.5 | 7.5 | 7.5 |
| Matting Agent[2] (Part by Weight) | 5.5 | 7.0 | 8.5 | 10.0 |
| Coating Activation component[3] | 1.8 | 1.8 | 1.8 | 1.8 |
| Coating Accelerator component[4] | 0.3 | 0.3 | 0.3 | 0.3 |
| Weight Mixing Ratio | 0.73 | 0.93 | 1.13 | 1.33 |
| Volume Mixing Ratio | 0.58 | 0.74 | 0.90 | 1.06 |
| Gloss at 60° | 73.9 | 44.7 | 13.2 | 1.8 |

[6]Yellow coating component was Imron ® Industrial Strength Yellow 9T03 ™, available from DuPont, Wilmington, USA, under respective registered or unregistered trademarks.
[2]-[4]Same as that in Table 1.

TABLE 4

Red Color Coating Mixture and Gloss Data.

|  | Ex. 13 | Ex. 14 | Ex. 15 | Ex. 16 |
|---|---|---|---|---|
| Red coating component[7] (Part by Weight) | 7.5 | 7.5 | 7.5 | 7.5 |
| Matting Agent[2] (Part by Weight) | 5.5 | 7.0 | 8.5 | 10.0 |
| Coating Activation component[3] | 1.8 | 1.8 | 1.8 | 1.8 |
| Coating Accelerator component[4] | 0.3 | 0.3 | 0.3 | 0.3 |
| Weight Mixing Ratio | 0.73 | 0.93 | 1.13 | 1.33 |
| Volume Mixing Ratio | 0.64 | 0.82 | 0.99 | 1.17 |
| Gloss at 60° | 54.5 | 7.5 | 0.9 | 0.6 |

[7]Red coating component was Imron ® Industrial Strength Red Oxide 9T12 ™, available from DuPont, Wilmington, USA, under respective registered or unregistered trademarks.
[2]-[4]Same as that in Table 1.

TABLE 5

Black Color Coating Mixture and Gloss Data.

|  | Ex. 17 | Ex. 18 | Ex. 19 | Ex. 20 | EX. 21 | EX. 22 |
|---|---|---|---|---|---|---|
| Black coating component[8] (Part by Weight) | 70 | 7.5 | 7.5 | 7.5 | 7.5 | 7.5 |
| Matting Agent[2] (Part by Weight) | 70 | 10 | 5.5 | 7.0 | 8.5 | 10 |
| Coating Activation component[3] | 18 | 1.8 | 1.8 | 1.8 | 1.8 | 1.8 |
| Coating Accelerator component[4] | 2.5 | 0 | 0.3 | 0.3 | 0.3 | 0.3 |
| Weight Mixing Ratio | 1.0 | 1.3 | 0.73 | 0.93 | 1.1 | 1.3 |
| Volume Mixing Ratio | 0.8 | 1.1 | 0.6 | 0.7 | 0.9 | 1.1 |
| Gloss at 60° | 20 | 1.2 | 79.6 | 50.7 | 6.5 | 0 |

[8]Black coating component was Imron ® Industrial Strength Black 9T02 ™, available from DuPont, Wilmington, USA, under respective registered or unregistered trademarks.
[2],[4]Same as that in Table 1.

TABLE 6

Densities of Compositions.

| Components | Density |
|---|---|
| White coating component[1] | 10.66 |
| Orange coating component[5] | 8.99 |
| Yellow coating component[6] | 8.64 |
| Red coating component[7] | 9.52 |
| Black coating component[8] | 8.69 |
| Matting Agent[2] | 10.85 |

[1], [2], and [5]-[8]Same as in Tables 1-5.

Examples 23-28

Gloss Value-Mixing Ratio Curve Fitting

Example 23

Figure 1A:
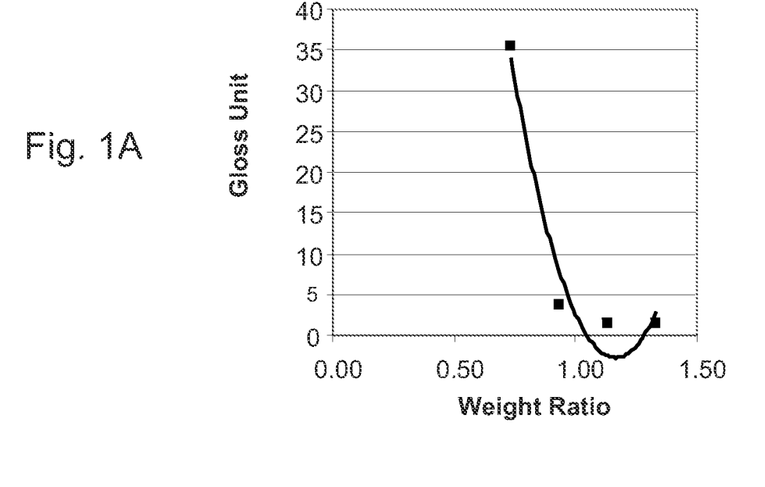

Data points of gloss values and weight mixing ratios of Examples 1-4 were plotted as shown in FIG. 1A. One of the best fitted curves has the following characteristics:

$$y=198.13x^2-461.41x+265.85$$

$$R^2=0.955. \quad (4)$$

Figure 1B:
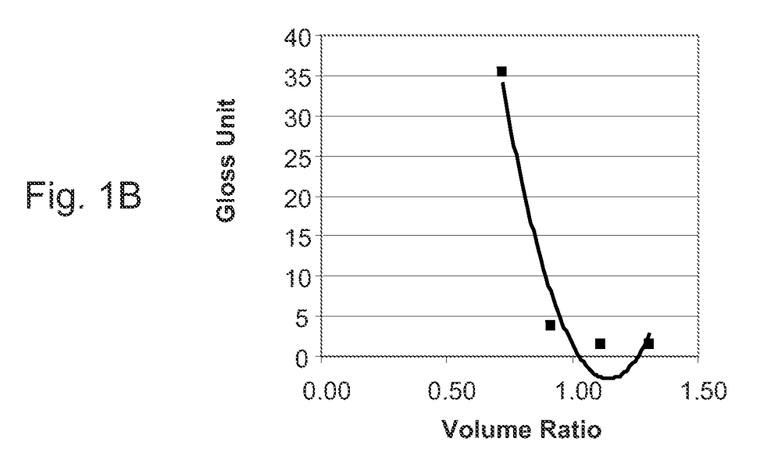

Data points of gloss values and volume mixing ratios of Examples 1-4 were plotted as shown in FIG. 18. One of the best fitted curves has the following characteristic's:

$$y=205.25x^2-469.63x+265.65$$

$$R^2=0.955. \quad (5)$$

Example 24

Figure 2A:
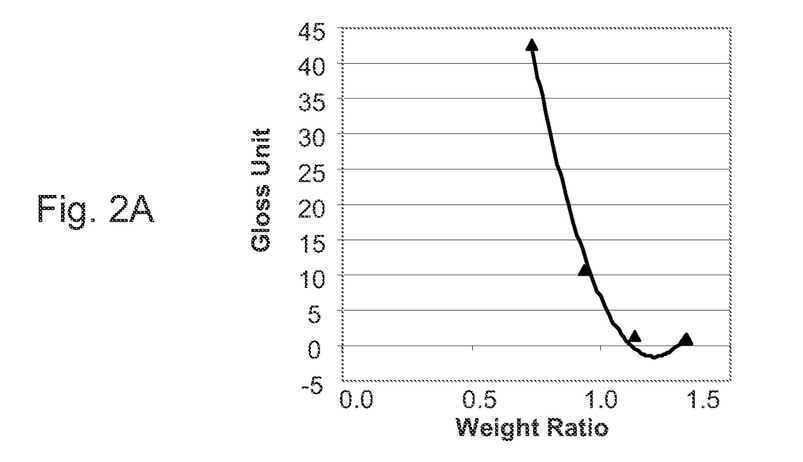

Data points of gloss values and weight mixing ratios of Examples 5-8 were plotted as shown in FIG. 2A. One of the best fitted curves has the following characteristics:

$$y=196.25x^2-472.78x+283.18$$

$$R^2=0.9918. \quad (6)$$

Figure 2B:
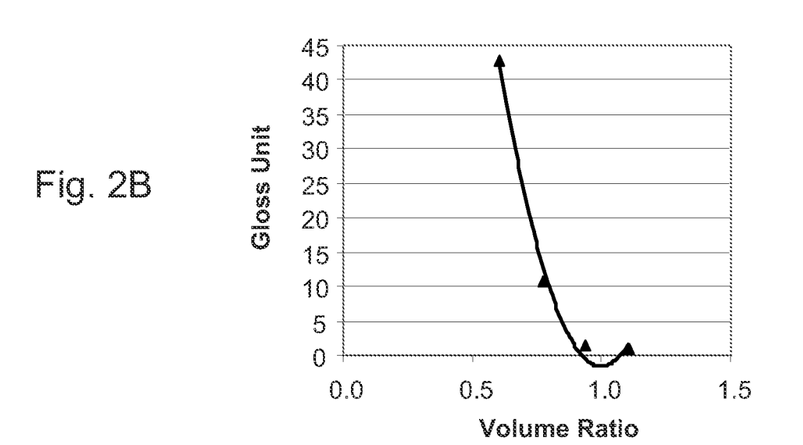

Data points of gloss values and volume mixing ratios of Examples 5-8 were plotted as shown in FIG. 28. One of the best fitted curves has the following characteristics:

$$y=285.86x^2-570.6x+283.18$$

$$R^2=0.9918. \quad (7)$$

Example 25

Figure 3A:
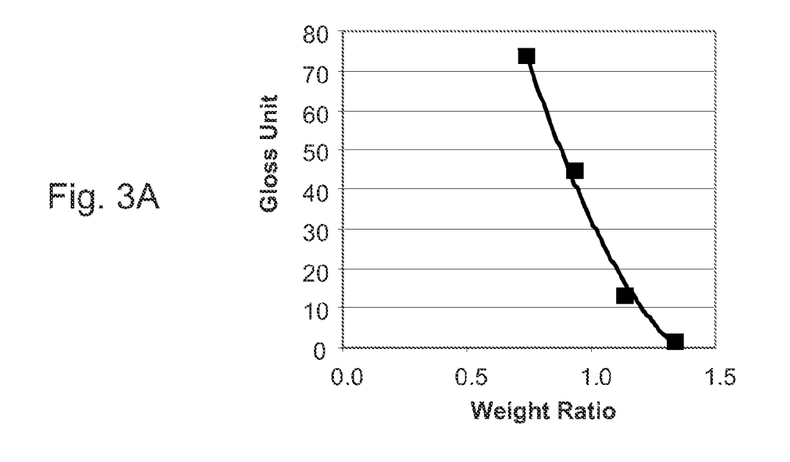

Data points of gloss values and weight mixing ratios of Examples 9-12 were plotted as shown in FIG. 3A. One of the best fitted curves has the following characteristics:

$$y=111.25x^2-353.82x+274.66$$

$$R^2=0.9921. \quad (8)$$

Figure 3B:
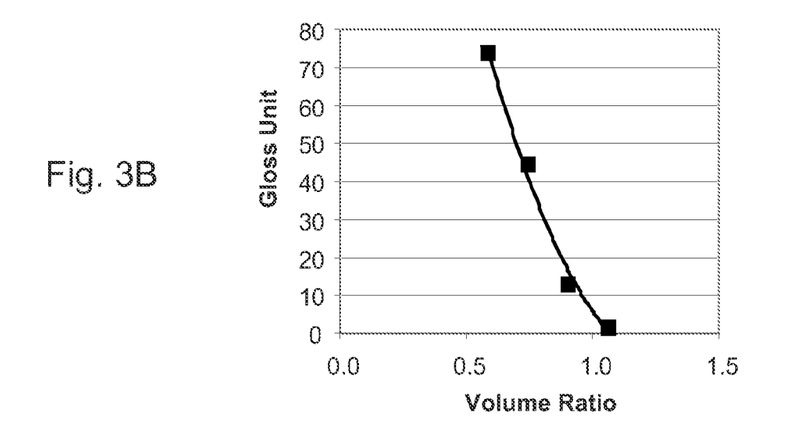

Data points of gloss values and volume mixing ratios of Examples 9-12 were plotted as shown in FIG. 36. One of the best fitted curve has the following characteristics:

$$y=175.44x^2-444.32x+274.66$$

$$R^2=0.9921. \quad (9)$$

Example 26

Figure 4A:
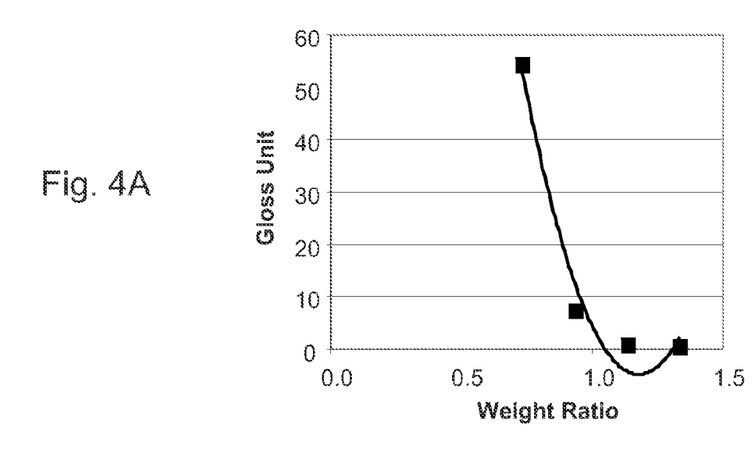

Data points of gloss values and weight mixing ratios of Examples 13-16 were plotted as shown in FIG. 4A. One of the best fitted curves has the following characteristics:

$$y=291.88x^2-687.36x+399.89$$

$$R^2=0.9712. \quad (10)$$

Figure 4B:
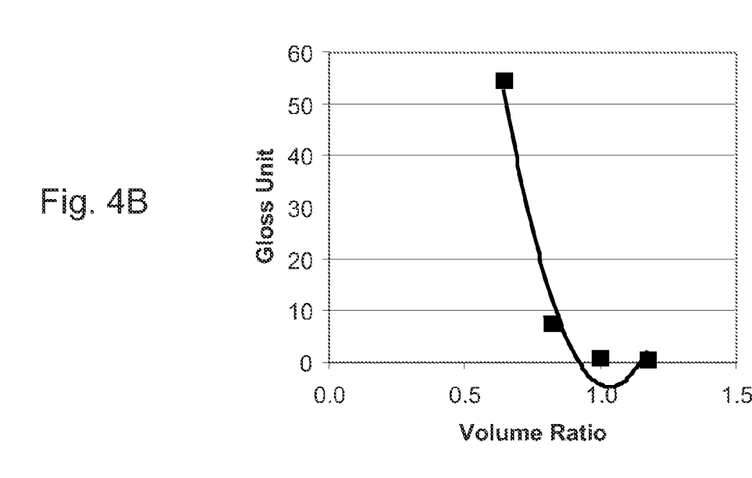

Data points of gloss values and volume mixing ratios of Examples 13-16 were plotted as shown in FIG. 4B. One of the best fitted curve has the following characteristics:

$$y=379.13x^2-783.39x+399.89$$

$$R^2=0.9712. \quad (11)$$

Example 27

Figure 5A:
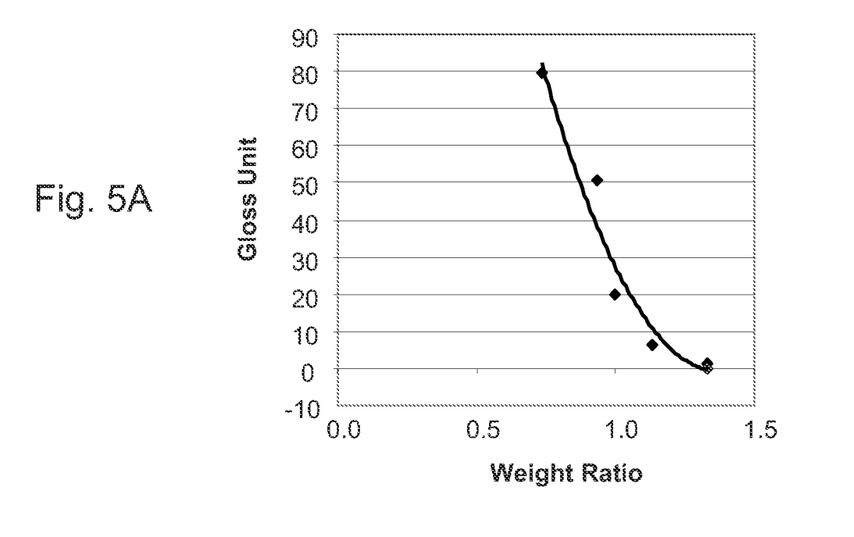

Data points of gloss values and weight mixing ratios of Examples 17-22 were plotted as shown in FIG. 5A. One of the best fitted curves has the following characteristics:

$$y=205.7x^2-563.02x+384.63$$

$$R^2=0.9548. \quad (12)$$

Figure 5B:
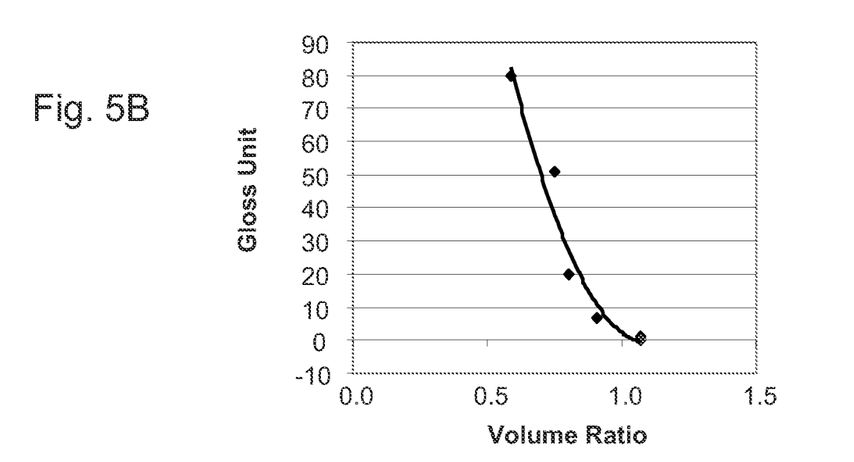

Data points of gloss values and volume mixing ratios of Examples 17-22 were plotted as shown in FIG. 56. One of the best fitted curves has the following characteristics.

$$y=320.66x^2-702.96x+384.63$$

$$R^2=0.9548. \quad (13)$$

Example 28

Figure 6A:
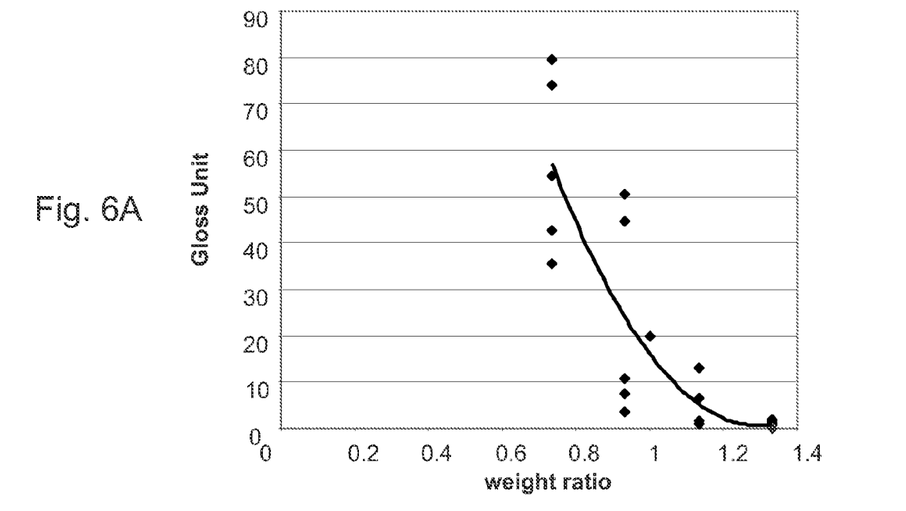

All data points of gloss values and weight mixing ratios from 5 different colors were plotted on one x-y chart as shown in FIG. 6A. One of the best fitted curves has the following characteristics:

$$y=181.79x^2-469.48x+303.75$$

$$R^2=0.7407. \tag{14}$$

Figure 6B:
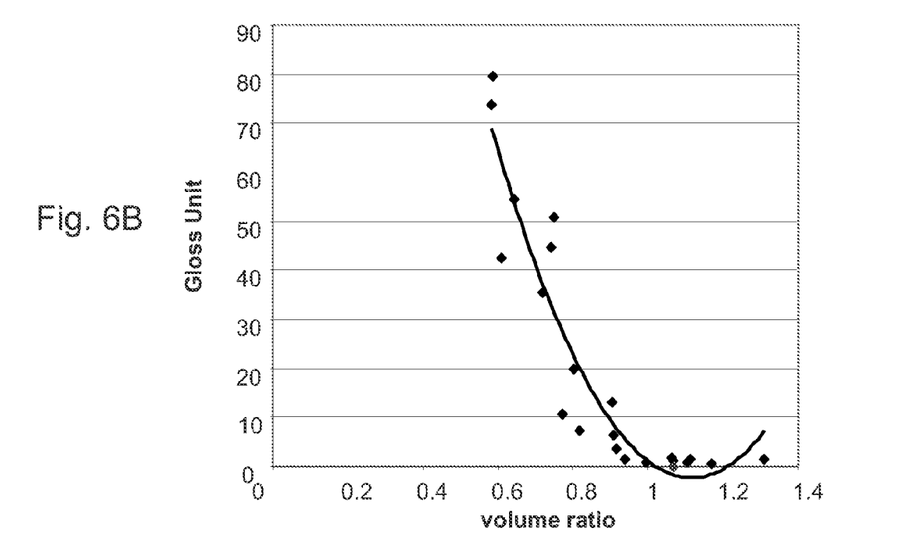

All data points of gloss values and volume mixing ratios from 5 different colors were plotted on one x-y chart as shown in FIG. 6B. One of the best fitted curves has the following characteristics:

$$y=251.51x^2-561.22x+310.8$$

$$R^2=0.8825. \tag{15}$$

What is claimed is:

1. A method for producing a coating having a target gloss value on a substrate, said coating is formed from a coating composition and a matting agent, said method comprising steps of:
   a) obtaining a gloss-mixing ratio correlation data system that comprises correlations of gloss values to mixing ratios of said matting agent and said coating composition;
   b) generating a target mixing ratio of said matting agent and said coating composition according to said target gloss value and said gloss-mixing ratio correlation data system;
   c) producing a coating mixture comprising said coating composition and said matting agent having said target mixing ratio; and
   d) producing said coating by applying said coating mixture over said substrate, wherein said gloss-mixing ratio correlation data system is generated by a fitting process comprising the steps of:
   i) producing a first coating mixture comprising said coating composition and said matting went according to a first mixing ratio $x_1$, applying the first coating mixture over a first substrate and allowing the first coating mixture to dry forming a dry first coating, and measuring a first gloss value $y_1$ of the dry first coating;
   ii) producing a second coating mixture comprising said coating composition and said matting agent according to a second mixing ratio $x_2$, applying the second coating mixture over a second substrate and allowing the second coating mixture to dry forming a dry second coating, and measuring a second gloss value $y_2$ of the dry second coating;
   iii) repeating the steps i) and ii) above for subsequent mixing ratios $x_3$ through $x_n$, and measuring subsequent gloss values $y_3$ through $y_n$; and
   iv) generating said gloss-mixing ratio correlation data system by fitting the mixing ratios) $x_1$ through $x_n$ and the gloss values $y_1$ through $y_n$;

wherein, n is an integer equal to or greater than 3, and said gloss-mixing ratio correlation data system has a correlation coefficient $R^2$ equal to or greater than 0.7, and wherein said gloss-mixing ratio correlation data system is expressed as a 2-degree polynomial fitting equation:

$$y=a_1x^2+a_2x+a_3 \tag{1}$$

wherein is a gloss value, x is a mixing ratio $a_1$, $a_2$ and $a_3$ are constants determined through fitting said mixing ratios $x_1$ through $x_n$ and said gloss values $y_1$ through $y_n$.

2. The method of claim 1, wherein said gloss-mixing ratio correlation data system is a gloss-mixing ratio plot chart in that said mixing ratios $x_1$ through $x_n$ and said gloss values $y_1$ through $y_n$ are plotted on an x-y chart and fitted to a fitting curve.

3. The method of claim 2, wherein said fitting curve is displayed on said x-y chart.

4. The method of claim 1, wherein said gloss-mixing ratio correlation data system has a correlation coefficient $R^2$ equal to or greater than 0.8.

5. The method claim 1, wherein said mixing ratios are selected from weight mixing ratios, volume mixing ratios, or a combination thereof.

6. The method of claim 1, wherein said mixing ratios are volume mixing ratios.

7. he method of claim 1 further comprising the step of curing said coating.

8. The method of claim 1, wherein said coating composition is selected from a solvent borne coating composition, a waterborne coating composition, or a powder coating composition.

9. The method of claim 1, wherein said coating composition is selected from a two-pack coating composition or a one-pack coating composition.

10. The method of claim 1, wherein said coating composition is selected from a chemical curable coating composition, a radiation curable coating composition, a chemical and radiation dual cure coating composition, or a lacquer coating composition.

11. The method of claim 1, wherein said substrate is selected from metal, wood, plastic, composite, or a combination thereof.

12. The method of claim 1, wherein said substrate is selected from a vehicle body, vehicle body part, or a combination thereof.

13. The method of claim 1, wherein said matting agent comprises silica.

14. The method of claim 1, wherein said matting agent comprises a polytrimethylene ether glycol having a Mn (number average molecular weight) in a range of from 500 to 10,000.

15. The method of claim 14, wherein said polytrimethylene ether glycol is polymerized from bio-derived 1,3-propanediol.

16. A method for producing a predicted gloss value of a coating on a substrate, said coating is formed from a coating composition and a matting agent, said method comprising steps of:
   a) obtaining a gloss-mixing ratio correlation data system that comprises correlations of gloss values to mixing ratios of said matting agent and said coating composition;
   b) providing a target mixing ratio;
   c) producing said predicted gloss value according to said gloss-mixing ratio correlation data system and said target mixing ratio; and
   d) outputting said predicted gloss value to an output device, wherein said gloss-mixing ratio correlation data system is generated by a fitting process comprising the steps of:
   i) producing a first coating mixture comprising said coating composition and said matting agent according to a first mixing ratio $x_1$, applying in the first coating mixture over a first substrate and allowing the first coating mixture to dry forming a dry first coating, and measuring a first gloss value $y_1$ of the dry first coating;
   ii) producing a second coating mixture comprising said coating composition and said matting agent according to a second mixing ratio $x_2$, applying the second coating mixture over a second substrate and allowing the second coating mixture to dry forming a dry second coating, and measuring a second gloss value $y_2$ of the dry second coating;

iii) repeating the steps i) and ii) above for subsequent mixing ratios $x_3$ through $x_n$ and measuring subsequent gloss values $y_3$ through $y_n$; and iv) generating said gloss-mixing ratio correlation data system by fitting he mixing ratios $x_1$ through $x_n$ and the gloss values $y_1$ through $y_n$;

wherein, n is an integer equal to or greater than 3, and said gloss-mixing ratio correlation data system has a correlation coefficient $R^2$ equal to or greater than 0.7, wherein said gloss-mixing ratio correlation data system is expressed as a 2-degree polynomial fitting equation:

$$y = a_1 x^2 + a_2 x + a_3 \tag{1}$$

wherein is a y loss value x is a mixin ratio $a_1$, $a_2$ and $a_3$ are constants determined through fitting said mixing ratios $x_1$ through $x_n$ and said gloss values $y_1$ through $y_n$.

17. The method of claim 16, wherein said gloss-mixing ratio correlation data system is a gloss-mixing ratio plot chart in that said mixing ratios $x_1$ through $x_n$ and said gloss values $y_1$ through $y_n$ are plotted on an x-y chart and fitted to a fitting curve.

18. The method of claim 17, wherein said fitting curve is displayed on said x-y chart.

19. The method of claim 16, wherein said gloss-mixing ratio correlation data system has a correlation coefficient $R^2$ equal to or greater than 0.8.

20. The method claim 16, wherein said mixing ratios are selected from volume mixing ratios, weight mixing ratios, or a combination thereof.

21. The method claim 16, wherein said mixing ratios are volume mixing ratios.

* * * * *